United States Patent [19]

Stapp

[11] 3,960,972

[45] June 1, 1976

[54] ALKENOL PRODUCTION

[75] Inventor: Paul R. Stapp, Bartlesville, Okla.

[73] Assignee: Phillips Petroleum Company, Bartlesville, Okla.

[22] Filed: Feb. 14, 1975

[21] Appl. No.: 549,889

[52] U.S. Cl. .......................... 260/638 R; 260/453 R; 260/465.6; 260/484 R; 260/488 H; 260/615 R; 260/617 R; 260/618 R; 260/633; 260/681
[51] Int. Cl.² .......................................... C07C 29/00
[58] Field of Search ..................... 260/638 R, 617 R

[56] References Cited
UNITED STATES PATENTS

| | | | |
|---|---|---|---|
| 2,335,027 | 11/1943 | Ritter | 260/638 R |
| 2,877,210 | 3/1959 | Bankert | 260/619 A |
| 2,932,671 | 4/1960 | Hager et al. | 260/619 A |
| 2,944,086 | 7/1960 | Coffield et al. | 260/619 A |
| 2,947,789 | 8/1960 | Ambelang | 260/619 A |
| 3,414,588 | 12/1968 | Jones | 260/638 R |

Primary Examiner—Joseph E. Evans

[57] ABSTRACT

The yield of alkenols is substantially improved by carrying out the reaction of olefins with formaldehyde in the presence of phenolic yield promoters. In accordance with one embodiment, alk-3-en-1-ols are produced in good yields from isobutylene and formaldehyde in the presence of 2,6-di-tert-butyl-4-methylphenol yield promoter.

6 Claims, No Drawings

ALKENOL PRODUCTION

This invention relates to an improved process for the production of alkenols. In accordance with another aspect, this invention relates to an improved process for producing increased yields of alkenols by the reaction of olefins with formaldehyde in the presence of selected phenolic yield promoters. In accordance with another aspect, this invention relates to an improved process for the production of increased yields of alkenols from formaldehyde and isobutylene in the presence of phenolic yield promoters.

Accordingly, an object of this invention is to provide an improved process for the production of alkenols. Another object of this invention is to provide novel yield promoters for increasing the yield of alkenols. A further object of this invention is to provide an economically feasible process for the production of alkenols whereby high yields of desired product are obtained.

Other objects, aspects, and the several advantages of the invention will be apparent to those skilled in the art upon reading the specification and the appended claims.

In accordance with the invention, it has been found that alkenols are obtained in high yields and high purity by reacting an olefin with formaldehyde in the presence of selected phenolic yield promoters.

In accordance with one specific embodiment, it has been found that alk-3-en-1-ols are obtained in high yields by reacting an olefin such as isobutylene with formaldehyde in the presence of at least one phenolic yield-promoting agent.

In accordance with a further embodiment of the invention, 3-methyl-3-buten-1-ols in high yield can be obtained by reacting isobutylene with formaldehyde in the presence of 2,6-di-tert-butyl-4-methylphenol yield promoter.

Olefinic compounds which are suitable for use in the instant invention are those having at least 1 allylic hydrogen, i.e., having the basic structure

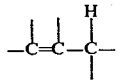

and from 3 to 20 carbon atoms per molecule. The olefinic double bond in such compounds can be part of a carbocyclic ring. Furthermore, substituents which are essentially inert under the reaction conditions can also be present in the olefinic reactant. Typical examples of such substituents include —CN, —Cl, —OCH$_3$, —CO$_2$CH$_2$CH$_3$, and the like. Of the olefinic reactants broadly suitable, the presently preferred olefinic compounds are those containing only carbon and hydrogen, such as the alkenes or cycloalkenes. Examples of suitable olefinic reactants include propylene, isobutylene, alpha-methylstyrene, 1-methyl-4-isopropenylcyclohexene, 1-methylcyclohexene, methallyl chloride, methyl isopropenyl ether, 5-methyl-5-hexenenitrile, and the like, and mixtures thereof.

Formaldehyde is employed as the aldehyde reactant in the instant invention. However, the formaldehyde reactant can be employed in any of its well-known commercially available forms, such as the cyclic trimer, 1,3,5-trioxane, or the polymeric form, paraformaldehyde, and the aqueous solution (commonly called Formalin) of about 37% concentration, which can contain methanol as an inhibitor.

As used herein, the term "phenolic" is intended to encompass phenols, 1-naphthols, and 2-naphthols.

The phenolic yield promoters of the instant invention are selected from the group consisting of phenols having the general formula

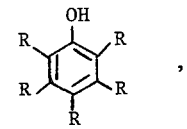

1-naphthols having the general formula

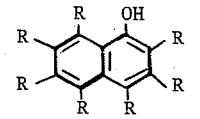

and 2-naphthols having the general formula

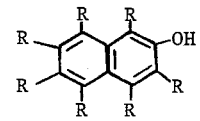

wherein R is selected from hydrogen, halogen, alkyl or alkoxy radicals having 1 to 10 carbon atoms, and other substituents which are essentially nonreactive with formaldehyde and/or the olefinic compound under the conditions employed.

The applicable phenols are further defined by the fact that positions 2-, 4-, and 6 on the ring must be occupied by a substituent other than hydrogen. Phenols suitable as yield promoters according to the instant invention are those which contain from 6 to 36 carbon atoms per molecule, preferably from 6 to 18 carbon atoms per molecule.

Examples of suitable phenols include 2-bromo-6-tert-butyl-4-nitrophenol; 4-bromo-2,6-di-tert-butylphenol; 4-bromo-2,6-diiodophenol; 2,6-di-tert-butyl-4-nonylphenol; pentabromophenol; pentachlorophenol; pentamethylphenol; pentafluorophenol; 2,3,4,6-tetramethylphenol; 2,4,6-tribromophenol; 2,4,6-tri-tert-butylphenol; 2,4,6-trichlorophenol; 2,6-di-tert-butyl-4-methylphenol; 2,4,6-tris(1-methylnonyl)phenol; and the like. Other suitable phenols include 4-bromo-3-methoxy-2,5,6-trimethylphenol, 4-tert-butoxy-2-tert-butyl-6-isopropylphenol, 4-tert-butoxy-2,6-di-tert-butylphenol, 4-tert-butyl-2,6-dimethoxyphenol, 2-bromo-4-tert-butyl-6-methoxyphenol, and 2,4,6-trimethoxyphenol. Mixtures of phenols can also be employed.

Suitable 1-naphthols for use in the instant invention can be described by the general formula

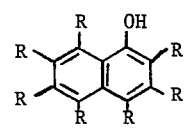

wherein R is selected from hydrogen, halogen, alkyl, or alkoxy radicals having 1–10 carbon atoms, and other substituents which are essentially nonreactive with formaldehyde and/or the olefinic compound under the conditions employed. The applicable 1-naphthols are further defined by the fact that positions 2- and 4- must be occupied by a substituent other than hydrogen. 1Naphthols suitable as yield promoters according to the instant invention are those which contain from 10–36 carbon atoms per molecule, preferably from 10–18 carbon atoms per molecule. Examples of suitable 1-naphthols include 2-tert-butyl-4-methoxy-1-naphthol, 2-chloro-4-methoxy-1-naphthol, 2,4-dibromo-1-naphthol, 2,4-dichloro-1-naphthol, 2,4-diethoxy-1-naphthol, 2,4-dimethoxy-1-naphthol, 2,4-dimethyl-1-naphthol, 4-methoxy-2-methyl-1-naphthol, 2,4,7-tribromo-1-naphthol, and the like.

Suitable 2-naphthols for use as yield promoters in the instant invention can be described by the general formula

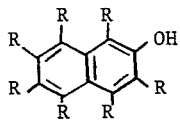

wherein R has the same meaning as employed in the general formula for the 1-naphthols. The applicable 2-naphthols are further defined by the fact that positions 1- and 3- must be occupied by substituents other than hydrogen. 2-Naphthols suitable as yield promoters according to the instant invention are those which contain from 10–36 carbon atoms per molecule, preferably from 10–18 carbon atoms per molecule. Examples of suitable 2-naphthols include 1,3-dibromo-2-naphthol, 1,3-dibromo-6-butyl-2-naphthol, 1,3-dibromo-6-ethyl-2-naphthol, 1,3-dibromo-6-hexyl-2-naphthol, 1,3-dibromo-6-pentyl-2-naphthol, 1,3-dibromo-6-propyl-2-naphthol, heptafluoro-2-naphthol, 6-bromo-1,3-dichloro-2-naphthol, 1,3-dimethyl-2-naphthol, 1,3,4-trichloro-2-naphthol, 1,3,6-tribromo-2-naphthol, and the like.

The molar ratio of olefinic reactant to formaldehyde for the reaction of the instant invention is broadly from about 1.5/1 up to about 15/1, preferably from 2/1 up to 11/1.

The reaction conditions, i.e., temperature and pressure, etc., employed in carrying out the invention are sufficient to cause reaction between the olefin and formaldehyde to produce alkenols. The temperature can be broadly from about 150°C to about 300°C, and preferably from 175°C–250°C. The time employed for the reaction for the instant invention can be from about 3 minutes up to 24 hours and preferably from 15 minutes to 8 hours.

The reaction of the instant invention is generally carried out under autogenous pressure but, if desired, pressure from an inert gas such as nitrogen or helium can also be applied up to about 1,000 psig of the inert gas.

The amount of yield promoter which is employed in the reaction of this invention is generally from about 0.5 to about 50 percent by weight, based on the formaldehyde charged to the reactor and preferably from five to 25 percent.

The reaction of formaldehyde with an olefinic compound in the presence of the above-described yield promoter is generally carried out in the presence of a diluent selected from compounds having from 1–20 carbon atoms per molecule. Examples of suitable diluents include cyclohexane, n-heptane, benzene, toluene, cumene, chlorobenzene, meta-dichlorobenzene, 1-chloronaphthalene, methoxybenzene, ethoxybenzene, diphenyl ether, 1-methoxynaphthalene, 1,2-dimethoxybenzene, dichloromethane, 1-chloro-4-methoxybenzene, diethyl ether, 4-chlorodiphenyl ether, chloroform, carbon tetrachloride, and the like. Mixtures of the above diluents can also be employed if desired.

The reaction mixtures obtained according to the process of the instant invention are usually distilled directly to yield unconsumed reactants which can be recycled to the reaction zone, products, and residue which generally contains the reaction promoter, which can also be recycled to the reaction zone. The reaction promoter can be recovered from the reaction mixture residue by simple fractional distillation or by selective extraction or by combination of such conventional processes.

The alkenols which are the principal products of the reaction according to the instant invention have utility in several areas of the chemical arts. They can be employed as blending agents for motor fuels or as solvents for lacquers, perfumes, and the like. They can be converted to halides or ethers, or nitrated for the production of diesel fuel ignition promoters. They can also be halogenated, oxidized, hydrogenated, or dehydrated, the latter operation producing conjugated diolefins which have important well-known uses in the art. A small amount of conjugated diolefin can sometimes be found in the products of the reaction according to the instant invention. Presumably, a small amount of the alkenol can be dehydrated in situ to form the diolefin in the reaction product. In addition, a small amount of the formate ester of the alkenol is usually produced along with the alkenol in the reaction according to the instant invention. Such esters can be separated from the alkenol and hydrolyzed to recover additional alkenol from the by-product formate ester if so desired.

EXAMPLE I

A series of runs was conducted in a 1-liter stainless steel autoclave equipped with stirring means. In each run the solvent (250 ml benzene), yield promoter (if added), and formaldehyde (paraformaldehyde 94%) were charged, the autoclave was sealed and flushed with nitrogen, and isobutylene was charged liquid phase from tared cylinders. In these runs the reaction was conducted at 200°C for 6 hours. The autoclave was vented after each run, the contents removed from the autoclave and fractionally distilled under nitrogen at atmospheric pressure. Product fractions were analyzed by gas-liquid phase chromotography. The results of these runs are presented in Table I below.

Table I

| Run No. | Moles $CH_2O$ | Moles i-$C_4H_8$ | Mole Ratio[d] | Yield Promoter,[a] g | % Yield Alkenol[b] | Ester[c] |
|---|---|---|---|---|---|---|
| 1 | 4.00 | 4.48 | 1.1 | 0 | 32 | 15 |
| 2 | 4.00 | 4.47 | 1.1 | 15 | 31 | 6 |
| 3 | 2.01 | 4.96 | 2.4 | 15 | 49 | 6 |
| 4 | 0.98 | 4.13 | 4.2 | 0 | 51 | 11 |
| 5 | 1.26 | 5.18 | 4.1 | 10 | 65 | 6 |
| 6 | 0.99 | 5.20 | 5.2 | 7.5 | 67 | 5 |
| 7 | 0.70 | 5.09 | 7.3 | 0 | 72 | 9 |

Table I-continued

| Run No. | Moles CH$_2$O | Moles i-C$_4$H$_8$ | Mole Ratio[d] | Yield Promoter,[a] g | % Yield Alkenol[b] | Ester[c] |
|---|---|---|---|---|---|---|
| 8 | 0.49 | 5.23 | 10.6 | 0 | 85 | 6 |

[a] 2,6-di-tert-butyl-4-methylphenol.
[b] 3-methyl-buten-1-ol.
[c] 3-methyl-3-buten-1-yl formate.
[d] isobutylene/formaldehyde.

The yields shown in Table I were calculated by dividing the moles of the product obtained by the moles of formaldehyde charged and multiplying by 100.

The above results demonstrate that improved yields of the desired alkenol are obtained by use of the phenol yield promoter provided the mole ratio of isobutylene to formaldehyde is above about 1.1. Furthermore, a plot of the alkenol yield vs. isobutylene/formaldehyde mole ratio with and without the yield promoter indicates that the resulting curves also appear to cross or become essentially the same at a mole ratio of isobutylene to formaldehyde of about 15/1.

EXAMPLE II

Two other runs were conducted in essentially the same manner as those of Example I but for a reaction time of 1 hour at 200°C. The results of these two runs are shown in Table II below.

Table II

| Run No. | Moles CH$_2$O | Moles i-C$_4$H$_8$ | Mole Ratio[d] | Yield Promoter,[a] g | % Yield Alkenol[b] | Ester[c] |
|---|---|---|---|---|---|---|
| 9 | 0.50 | 4.96 | 9.9 | 0 | 30 | 1 |
| 10 | 0.50 | 5.18 | 10.3 | 1 | 58 | 2 |

[a] 2,6-di-tert-butyl-4-methylphenol.
[b] 3-methyl-3-buten-1-ol.
[c] 3-methyl-3-buten-1-yl formate.
[d] isobutylene/formaldehyde.

These results also demonstrate the significant improvement in alkenol yield obtained in the presence of the yield-promoting phenol at a mole ratio of isobutylene to formaldehyde of about 10.

I claim:

1. A process for the production of alkenols or cycloalkenols which comprises reacting
   a. at least one olefinic compound selected from the group consisting of alkenes and cycloalkenes having from 3 to 20 carbon atoms per molecule and at least one allylic hydrogen with
   b. formaldehyde in the presence of
   c. a yield-promoting amount ranging from about 0.5 to about 50 percent by weight based on formaldehyde charged to the reaction of at least one phenolic compound selected from the group consisting of phenols, 1-naphthols, and 2-naphthols having the general formula

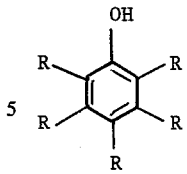, 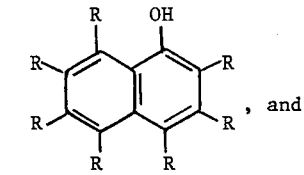

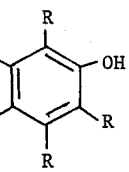

wherein R is selected from hydrogen, halogen, alkyl, and alkoxy radicals having 1 to 10 carbon atoms, with the further proviso that the phenol contain a total of from 6 to 36 carbon atoms per molecule and that positions 2-, 4-, and 6- on the ring must be occupied by a substituent other than hydrogen, said reacting being effected under reaction conditions including an elevated temperature and pressure sufficient to produce alkenols or cycloalkenols.

2. A process according to claim 1 wherein said reacting is carried out at a temperature in the range from about 150°C to about 300°C and under autogenous pressure with an amount of said phenolic promoting agent ranging from 5 to 25 percent by weight based on the formaldehyde charged to the reaction and a molar ratio of (a) to (b) in the range of from about 1.5:1 to 15:1.

3. A process according to claim 1 wherein said reacting is carried out in an inert reaction diluent.

4. A process according to claim 1 for the production of 3-methyl-3-buten-1-ol which comprises reacting isobutylene with formaldehyde in benzene as the reaction medium in the presence of 2,6-di-tert-butyl-4-methylphenol.

5. A process according to claim 1 for the production of 3-methyl-3-buten-1-ol which comprises reacting (a) isobutylene with (b) formaldehyde at a temperature in the range of about 150°C to about 300°C under autogenous pressure in the presence of (c) 2,6-di-tert-butyl-4-methylphenol in an amount of (c) ranging from 5 to 25 percent by weight based on formaldehyde charged to the reaction.

6. A process according to claim 1 wherein said phenol has the formula

* * * * *